(12) United States Patent
Ma et al.

(10) Patent No.: US 11,060,080 B2
(45) Date of Patent: Jul. 13, 2021

(54) METHOD FOR FERMENTATION-PRODUCTION OF PENTANEDIAMINE COMPRISING CARBON DIOXIDE STRIPPING TECHNIQUE

(71) Applicant: HEILONGJIANG EPPEN NEW MATERIALS CO., LTD., Heilongjiang (CN)

(72) Inventors: Jiyin Ma, Ningxia (CN); Tingyi Wen, Ningxia (CN); Shuwen Liu, Ningxia (CN); Yong Liang, Ningxia (CN); Daihuan Li, Ningxia (CN); Yun Zhang, Ningxia (CN); Xiuling Shang, Ningxia (CN); Chunguang Zhao, Ningxia (CN); Xiaowei Guo, Ningxia (CN); Gang Meng, Ningxia (CN)

(73) Assignee: HEILONGJIANG EPPEN NEW MATERIALS CO., LTD., Daqing (CN)

( * ) Notice: Subject to any disclaimer, the term of this patent is extended or adjusted under 35 U.S.C. 154(b) by 79 days.

(21) Appl. No.: 16/311,707

(22) PCT Filed: May 16, 2017

(86) PCT No.: PCT/CN2017/084552
§ 371 (c)(1),
(2) Date: Dec. 20, 2018

(87) PCT Pub. No.: WO2017/198147
PCT Pub. Date: Nov. 23, 2017

(65) Prior Publication Data
US 2019/0322995 A1    Oct. 24, 2019

(30) Foreign Application Priority Data

May 16, 2016   (CN) .......................... 201610322421.5

(51) Int. Cl.
| | |
|---|---|
| *C12P 13/08* | (2006.01) |
| *C12N 9/88* | (2006.01) |
| *B01D 1/18* | (2006.01) |
| *B01D 3/06* | (2006.01) |
| *B01D 19/00* | (2006.01) |
| *C12P 13/00* | (2006.01) |
| *C12R 1/19* | (2006.01) |
| *A61K 38/00* | (2006.01) |

(52) U.S. Cl.
CPC ............... *C12N 9/88* (2013.01); *B01D 1/18* (2013.01); *B01D 3/06* (2013.01); *B01D 19/0036* (2013.01); *B01D 19/0073* (2013.01); *C12P 13/001* (2013.01); *C12R 1/19* (2013.01); *C12Y 401/01018* (2013.01)

(58) Field of Classification Search
CPC ..... C12P 7/14; C12P 13/08; C12Y 401/01018
See application file for complete search history.

(56) References Cited

U.S. PATENT DOCUMENTS

| | | | | |
|---|---|---|---|---|
| 5,489,623 A | * | 2/1996 | Babb | C07C 43/225 522/151 |
| 7,189,543 B2 | | 3/2007 | Nishi et al. | |
| 2008/0207901 A1 | * | 8/2008 | Schneider | C07D 251/70 544/204 |
| 2010/0292429 A1 | | 11/2010 | Voelkert et al. | |
| 2014/0131191 A1 | * | 5/2014 | Tachikawa | B01D 3/007 203/26 |
| 2017/0226544 A1 | | 8/2017 | Wen et al. | |
| 2017/0369913 A1 | * | 12/2017 | Suominen | C12Y 402/01001 |

FOREIGN PATENT DOCUMENTS

| | | |
|---|---|---|
| CN | 101578256 A | 11/2009 |
| CN | 101981202 A | 2/2011 |
| CN | 102056889 B | 1/2016 |
| CN | 105316270 A | 2/2016 |
| CN | 105861586 A | 8/2016 |
| EP | 1482055 A1 | 12/2004 |
| JP | 2008193898 A | 8/2008 |
| WO | WO-2006123778 A1 * | 11/2006 ............ C12P 13/001 |
| WO | 2011129293 A1 | 10/2011 |

OTHER PUBLICATIONS

International Search Report of PCT/CN2017/084552 dated Aug. 16, 2017.
Written Opinion of PCT/CN2017/084552 dated Aug. 16, 2017.
Stefanie Kind et al., From zero to hero—Production of bio-based nylon from renewable resources using engineered Corynebacterium glutamicum, Metabolic Engineering, 2014, vol. 25, pp. 113-123.
Zhang, Guoqiang et al., A Mimicking-of-DNA-Methylation-Patterns Pipeline for Overcoming the Restriction Barrier of Bacteria, PLOS Genetics, Sep. 2012, vol. 8, Issue 9, e1002987.
Li, Dondxia et al., Progress in biosythesis of diaminopentane, Chinese Journal of Biotechnology, Feb. 25, 2014, vol. 30, No. 2, pp. 161-1746.
Zhu, Jing, Study of the Conversion of L-Lysine into Cadaverine in a Microorganism, Master Thesis, Dec. 31, 2010, Tianjin University of Science and Technology.
First Office Action of Counterpart Chinese Patent Application No. 201610322421.5 dated Jan. 13, 2017.

* cited by examiner

*Primary Examiner* — Scarlett Y Goon
*Assistant Examiner* — Samuel W Liu (57) ABSTRACT

A method for fermentation-production of a pentanediamine, comprising: culturing a cell expressing a lysine decarboxylase to obtain a whole cell fermentation broth comprising a pentanediamine; and extracting the pentanediamine from the whole cell fermentation broth, and striping the whole cell fermentation broth of carbon dioxide contained therein before adding a strong base. The method greatly increases a production volume of the pentanediamine.

8 Claims, 3 Drawing Sheets
Specification includes a Sequence Listing.

SEQUENCE LISTING

<160> NUMBER OF SEQ ID NOS: 12

<210> SEQ ID NO 1

<211> LENGTH: 2148
<212> TYPE: DNA
<213> ORGANISM: Escherichia coli

<400> SEQUENCE: 1

```
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac     120
gacttattaa aactgatcga aaacaatgcg cgtctgtgcg gcgttatttt tgactgggat     180
aaatataatc tcgagctgtg cgaagaaatt agcaaaatga cgagaaccct gccgttgtac     240
gcgttcgcta atacgtattc cactctcgat gtaagcctga atgacctgcg tttacagatt     300
agcttctttg aatatgcgct gggtgctgct gaagatattg ctaataagat caagcagacc     360
actgacgaat atatcaacac tattctgcct ccgctgacta agcactgtt taaatatgtt      420
cgtgaaggta aatatacttt ctgtactcct ggtcacatgg gcggtactgc attccagaaa     480
agcccggtag gtagcctgtt ctatgatttc tttggtccga ataccatgaa atctgatatt     540
tccatttcag tatctgaact gggttctctg ctggatcaca gtggtccaca caagaagca      600
gaacagtata tcgctcgcgt cttaacgca gaccgcagct acatggtgac caacggtact      660
tccactgcga acaaaattgt tggtatgtac tctgctccag caggcagcac cattctgatt     720
gaccgtaact gccacaaatc gctgacccac ctgatgatga tgagcgatgt tacgccaatc     780
tatttccgcc cgacccgtaa cgcttacggt attcttggtg tatcccaca gagtgaattc      840
cagcacgcta ccattgctaa gcgcgtgaaa gaaacaccaa acgcaacctg gccggtacat     900
gctgtaatta ccaactctac ctatgatggt ctgctgtaca acaccgactt catcaagaaa     960
acactggatg tgaaatccat ccactttgac tccgcgtggg tgccttacac caacttctca    1020
ccgattacg aaggtaaatg cggtatgagc ggtggccgtg tagaagggaa agtgatttac     1080
gaaacccagt ccactcacaa actgctggcg gcgttctctc aggcttccat gatccacgtt    1140
aaaggtgacg taaacgaaga aacctttaac gaagcctaca tgatgcacac caccacttct    1200
ccgcactacg gtatcgtggc gtccactgaa accgctgcgg cgatgatgaa aggcaatgca    1260
ggtaagcgtc tgatcaacgg ttctattgaa cgtgcgatca aattccgtaa agagatcaaa    1320
cgtctgagaa cggaatctga tggctggttc tttgatgtat ggcagccgga tcatatcgat    1380
acgactgaat gctggccgct gcgttctgac agcacctggc acggcttcaa aaacatcgat    1440
aacgagcaca tgtatcttga cccgatcaaa gtcaccctgc tgactccggg gatggaaaaa    1500
gacggcacca tgagcgactt tggtattccg ccagcatcg tggcgaaata cctcgacgaa     1560
catggcatcg ttgttgagaa accggtccg tataacctgc tgttcctgtt cagcatcggt     1620
atcgataaga ccaaagcact gagcctgctg cgtgctctga ctgactttaa acgtgcgttc    1680
gacctgaacc tgcgtgtgaa aaacatgctg ccgtctctgt atcgtgaaga tcctgaattc    1740
tatgaaaaca tgcgtattca ggaactggct cagaatatcc acaaactgat tgttcaccac    1800
aatctgccgg atctgatgta tcgcgcattt gaagtgctgc cgacgatggt aatgactccg    1860
tatgctgcat tccagaaaga gctgcacggt atgaccgaag aagtttacct cgacgaaatg    1920
gtaggtcgta ttaacgccaa tatgatcctt ccgtacccgc cggagttcc tctggtaatg     1980
ccgggtgaaa tgatcaccga agaaagccgt ccggttctgg agttcctgca gatgctgtgt    2040
gaaatcggcg ctcactatcc gggctttgaa accgatattc acggtgcata ccgtcaggct    2100
gatggccgct ataccgttaa ggtattgaaa gaagaaagca aaaaataa                 2148
```

```
<210> SEQ ID NO 2
<211> LENGTH: 510
<212> TYPE: DNA
<213> ORGANISM: Escherichia coli

<400> SEQUENCE: 2
cgcggatcct gcgccattct caacatcctt tagatgaaaa acaattagca gcactgaaca      60
cagaaataga taacattgtt acactaccgg aattgaataa cctgtccatt atatatcaaa    120
taaaagcggt cagtgctctg gtaaaaggta aacagatga gtcttaccag gcgataaata    180
ctggcattga tcttgaaatg tcctggctaa attatgtatt gcttggcaag gtttatgaaa    240
tgaaggggat gaaccgggaa gcggctgatg catatctcac cgcctttaat ttacgcccag    300
gggcaaacac cctttactgg attgaaaatg gtatattcca gacttctgtt ccttatgttg    360
taccttatct cgacaaattt ctcgcttcag aataagtaac tcccggttg atttatgctc    420 ggcaatattt gttgttgagt ttttgtatgt tactgttggt ataatatgtt gcggcataat    480
acgactcact ataggggaat tgtgagcgga                                     510

<210> SEQ ID NO 3
<211> LENGTH: 610
<212> TYPE: DNA
<213> ORGANISM: Escherichia coli

<400> SEQUENCE: 3
actcactata ggggaattgt gagcggataa caattccgaa attaggagaa gagcatgagt      60
tctgccaaga agatcgggct atttgcctgt accggtgttg ttgccggtaa tatgatgggg    120
agcggtattg cattattacc tgcgaaccta gcaagtatcg gtggtattgc tatctggggt    180
tggattatct ctattattgg tgcaatgtcg ctggcgtatg tatatgcccg actggcaaca    240 aaaaaccgc aacaaggtgg cccaattgct tatgccggag aaatttcccc tgcatttggt    300
tttcagacag gtgttcttta ttaccatgct aactggattg gtaacctggc gattggtatt    360
accgctgtat cttatctttc caccttcttc ccagtattaa atgatcctgt tccggcgggt    420
atcgcctgta ttgctatcgt ctgggtattt accttttgtaa atatgctcgg cggtacctgg    480
gtaagccgtt taaccactat tggtctggtg ctggttctta ttcctgtggt gatgactgct    540
attgttggct ggcattggtt tgatgcggca acttatgcag ctaactggaa tactgcggag    600
cggccgcaat                                                           610

<210> SEQ ID NO 4
<211> LENGTH: 1080
<212> TYPE: DNA
<213> ORGANISM: Escherichia coli

<400> SEQUENCE: 4
cgcggatcct gcgccattct caacatcctt tagatgaaaa acaattagca gcactgaaca      60
cagaaataga taacattgtt acactaccgg aattgaataa cctgtccatt atatatcaaa    120
taaaagcggt cagtgctctg gtaaaaggta aacagatga gtcttaccag gcgataaata    180
ctggcattga tcttgaaatg tcctggctaa attatgtatt gcttggcaag gtttatgaaa    240
tgaaggggat gaaccgggaa gcggctgatg catatctcac cgcctttaat ttacgcccag    300
gggcaaacac cctttactgg attgaaaatg gtatattcca gacttctgtt ccttatgttg    360
taccttatct cgacaaattt ctcgcttcag aataagtaac tcccggttg atttatgctc    420 ggcaatattt gttgttgagt ttttgtatgt tactgttggt ataatatgtt gcggcataat    480
```

```
acgactcact ataggggaat tgtgagcgga taacaattcc gaaattagga gaagagcatg      540
agttctgcca agaagatcgg gctatttgcc tgtaccggtg ttgttgccgg taatatgatg      600
gggagcggta ttgcattatt acctgcgaac ctagcaagta tcggtggtat tgctatctgg      660
ggttggatta tctctattat tggtgcaatg tcgctggcgt atgtatatgc ccgactggca      720
acaaaaaacc cgcaacaagg tggcccaatt gcttatgccg gagaaatttc ccctgcattt      780
ggttttcaga caggtgttct ttattaccat gctaactgga ttggtaacct ggcgattggt      840
attaccgctg tatcttatct ttccaccttc ttcccagtat aaatgatcc tgttccggcg      900 ggtatcgcct gtattgctat cgtctgggta tttacctttg taaatatgct cggcggtacc      960
tgggtaagcc gtttaaccac tattggtctg gtgctggttc ttattcctgt ggtgatgact     1020
gctattgttg gctggcattg gtttgatgcg gcaacttatg cagctaactg gaatactgcg     1080
```

```
<210> SEQ ID NO 5
<211> LENGTH: 41
<212> TYPE: DNA
<213> ORGANISM: Artificial Sequence
<220> FEATURE:
<223> OTHER INFORMATION: Synthetic

<400> SEQUENCE: 5
catgccatgg cagttattgc aatattgaat catatgggag t                          41

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
acgcgtcgac ctccttatga gcaaaaaagg gaagtg                                36

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
cgcggatcct gcgccattct caacatcctt                                       30

<210> SEQ ID NO 8
<211> LENGTH: 58
<212> TYPE: DNA
<213> ORGANISM: Artificial Sequence
<220> FEATURE:
<223> OTHER INFORMATION: Synthetic

<400> SEQUENCE: 8
tccgctcaca attcccctat agtgagtcgt attatgccgc aacatattat accaacag        58

<210> SEQ ID NO 9
<211> LENGTH: 59
<212> TYPE: DNA
<213> ORGANISM: Artificial Sequence
<220> FEATURE:
<223> OTHER INFORMATION: Synthetic

<400> SEQUENCE: 9
actcactata ggggaattgt gagcggataa caattccgaa attaggagaa gagcatgag       59
```

```
<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
attgcggccg ctccgcagta ttccagttag ct                                 32

<210> SEQ ID NO 11
<211> LENGTH: 46
<212> TYPE: DNA
<213> ORGANISM: Artificial Sequence
<220> FEATURE:
<223> OTHER INFORMATION: Synthetic

<400> SEQUENCE: 11
taatacgact cactataggg gaattgtgag cggataacaa ttcccc                  46

<210> SEQ ID NO 12
<211> LENGTH: 47
<212> TYPE: DNA
<213> ORGANISM: Artificial Sequence
<220> FEATURE:
<223> OTHER INFORMATION: Synthetic

<400> SEQUENCE: 12
tctagaaata attttgttta actttaagaa ggagatatac catgggc                 47
```

METHOD FOR FERMENTATION-PRODUCTION OF PENTANEDIAMINE COMPRISING CARBON DIOXIDE STRIPPING TECHNIQUE

The present application claims priority of Chinese Patent Application No. CN201610322421.5, filed on May 16, 2016, the contents of which are incorporated herein by reference in their entireties.

REFERENCE TO SEQUENCE LISTING

The substitute Sequence Listing is submitted to replace the previously submitted sequence listing as an ASCII formatted text file via EFS-Web, with a file name of "Substitute_Sequence_Listing.TXT", a creation date of Jul. 14, 2020, and a size of 7,801 bytes. The Substitute_Sequence_Listing filed via EFS-Web is part of the specification and is incorporated in its entirety by reference herein.

FIELD OF THE INVENTION

The present invention relates to the field of biological fermentation engineered, specifically relates to a biocatalytic process for producing 1,5-pentanediamine and separation and extraction technology thereof, i.e., a technique for separating and extracting pentanediamine from whole-cell catalytic liquid by carbon dioxide removal method.

BACKGROUND OF THE INVENTION 1,5-Pentanediamine, also known as Cadaverine, 1,5-Diaminopentane, can be polymerized into polymer polyamide materials (i.e. nylon) with diprotic acid. The global production of about 7 million tons of polyamide materials annually consumes a large amount of petrochemical resources, so the synthesis of 1,5-pentanediamine, an important constituent monomer of polyamides, by biological method, has important economic and ecological significance.

Whole-cell catalysis uses lysine as a substrate to catalyze the production of pentanediamine by lysine decarboxylase in cells. At present, lysine, as one of the major amino acid varieties, has a serious overcapacity and very low profit margin. Therefore, the development of an efficient biocatalytic production method of pentanediamine with lysine as substrate can not only develop new bio-based material market, but also promote the transformation and upgrading of the amino acid fermentation industry.

Regarding to the prior art for separating and extracting pentanediamine from a fermentation broth/whole-cell catalytic solution, the following reports can be cited. U.S. Pat. No. 7,189,543B2 discloses a process for preparing pentanediamine adipate crystals directly from a catalytic solution. Pentanediamine adipate solution with a pH value of 6.0 is obtained by neutralizing pentanediamine produced in whole-cell catalytic process with adipic acid. Cells in the pentanediamine catalytic solution are removed, and the solution is decolorized with activated carbon and concentrated to a salt content of 70-77%. Pentanediamine adipate crystals which is used in nylon polymerization are obtained after cooling. The patents (US2010/0292429A1, CN101981202A and EP1482055A1) and the literature (Metabolic Engineered, 2014, 25: 113-123) disclose the application of butanol extraction method in the separation and extraction of pentanediamine from a fermentation broth. Sodium hydroxide is added into the pentanediamine fermentation broth. After refluxing at high temperature the by-products in the fermentation broth are pyrolysed, and then the organic phase containing pentanediamine is obtained by multiple extraction with butanol, and the low boiling point solvent in the organic phase is distilled off to obtain the high boiling point pentanediamine. The pentanediamine of high purity is obtained by further distillation.

Among the prior art for the separation and extraction of pentanediamine, crystallization method has low yield and the product remains impurities such as lysine, which is difficult to further refine, and the obtained pentanediamine carboxylate produces surface appearance defects such as fisheye when used as polyamide resin membrane material, and the fluidity of injection molding is also affected (CN101578256A). The yield of pentanediamine obtained by extraction method is low; the purity of pentanediamine products are reduced by residual organic solvents; the organic solvents have high odor, high toxicity, inflammable and explosive, which increase the operation difficulty of practical application; organic solvents need to be recycled, which increase the process flow and energy consumption.

BRIEF DESCRIPTION OF THE INVENTION

The technical problem to be solved by the present invention is to provide a new fermentation method for the preparation of 1,5-pentanediamine, which can increase the amount of 1,5-pentanediamine, and/or reduce the amount of strong base and the production of salt residue, thereby reducing the comprehensive cost of the production of pentanediamine. Specifically, the method according to the present invention includes:
(1) culturing a cell expressing a lysine decarboxylase to obtain a fermentation broth comprising 1,5-pentanediamine; and
(2) extracting the 1,5-pentanediamine in the fermentation broth obtained in the step (1), wherein carbon dioxide therein is removed before adding a strong base into the fermentation broth.

Preferably, in step (1) of the method according to the present invention, the cell is a cell overexpressing lysine decarboxylase, and preferably a cell with enhanced lysine decarboxylase gene expression (for example, the expression of lysine decarboxylase gene is enhanced by replacing the promoter of lysine decarboxylase gene with a strong promoter (for example, T7 promoter)).

It is also preferred that in step (1) of the method according to the present invention, the cell is a bacterial cell, preferably an *E. coli* cell, such as *E. coli* BL21 (DE3).

It is also preferred that in step (1) of the method according to the present invention, no acidic pH regulator is added to the culture, and the cells themselves generate $CO_2$ to neutralize 1,5-pentanediamine.

In addition, it is preferred that in step (1) of the method according to the present invention, the bacteria produce 1,5-pentadiamine under catalyzation by lysine decarboxylase with lysine as a substrate.

Preferably, step (2) according to the method of the present invention comprising:
(21) separating (e.g., centrifuging or filtering) the liquid from the fermentation broth;
(22) removing carbon dioxide from the liquid obtained in step (21), and then adding a base for treatment; and
(23) extracting a composition (e.g., a fraction) containing 1,5-pentanediamine from the treatment liquid obtained in step (22).

More preferably, in step (22) of the method according to the present invention, carbon dioxide in the liquid is removed by decompressing and/or heating to separate the carbon dioxide in the liquid.

It is also more preferred that in step (22) of the method according to the present invention, the base includes sodium hydroxide, potassium hydroxide and/or calcium hydroxide.

More preferably, in step (23) of the method according to the present invention, the extracting includes distilling (such as atmospheric distilling, reduced pressure distilling and/or rectifying), evaporating (e.g., flash evaporating) and/or drying (e.g. spray drying and/or reduced pressure drying).

Preferably, in the method according to the present invention, the output of 1,5-pentanediamine is greater than 30 g/L of the fermentation broth, preferably greater than 50 g/L of the fermentation broth, more preferably greater than 80 g/L of the fermentation broth, more preferably greater than 100 g/L of the fermentation broth, most preferably greater than 120 g/L of the fermentation broth.

DETAILED DESCRIPTION OF THE INVENTION

In the previous stage, a whole-cell catalytic production process for pentanediamine using self-controlled pH by by-product carbon dioxide has been established by the inventor of the present invention. In theory, the catalytic reaction solution contains equimolar amounts of pentanediamine and carbon dioxide (carbonate ion).

Further research by the inventor shows that the carbon dioxide generated during the decarboxylation of lysine for pentanediamine in the whole-cell catalytic solution can be removed under reduced pressure and heating treatment, thus increasing the pH value of the catalytic solution; when the strong base is further used to adjust the catalytic solution to reach the same alkaline condition, the amount of the base is obviously reduced after the removal of carbon dioxide, and the distillation yield of pentanediamine is significantly increased, subsequently. On this basis, a method for separating and extracting pentanediamine from pentanediamine salt ionic catalytic solution is established, and the present invention is completed.

The method for separating and extracting pentanediamine from the whole-cell catalytic solution provided by the present invention comprises the following steps:
(1) removing bacterial cells in the pentanediamine catalytic solution to obtain a clear liquid of the catalytic solution;
(2) removing part of the carbon dioxide in the clear liquid;
(3) adding a strong base into the clear liquid after the carbon dioxide is removed;
(4) distilling and collecting to obtain pentanediamine.

The bacterial cells in the catalytic liquid is removed by the chemical principle of solid-liquid separation and the clear liquid is collected. Specific methods for removing cells from the catalytic solution include flocculation, sedimentation, centrifugation or filtration, etc.

Since carbon dioxide is an acidic gas, basic pentanediamine can act as a chemical absorbent for carbon dioxide, and reversibly react to form a water-soluble salt. Temperature change has a great influence on the reversible reaction. Low temperature is favorable for the reaction to proceed to the direction of producing the weak-acid-weak-base-salt, while high temperature can decompose the weak-acid-weak-base-salt and release carbon dioxide. The inventor further finds that reducing the pressure is also beneficial for the removal of carbon dioxide from pentanediamine solution. Simultaneous reducing the pressure and heating can quickly remove carbon dioxide from the pentanediamine catalyst solution. Among them, the decomposition temperature of carbon dioxide is between 40-2000, and the distillation pressure (absolute pressure) is between 0.2 kPa-1100 kPa.

It should be noted that although increasing the temperature can improve the removal efficiency of carbon dioxide, it will also lead to the volatilization of pentanediamine and increase the loss rate of product. During the experiments, the inventor found that the volatile pentanediamine and carbon dioxide gas condensed on the surface of the equipment pipeline to form milky white pentanediamine carbonate when the distillation pressure is between 20-200 kPa and the heating temperature is over 120° C. This will not only reduce the yield of pentanediamine, and increase the production cost of pentanediamine, but also lead to blockage of equipment pipeline, and increase the operation difficulty in production and application. Considering the cost and maneuverability of actual production and application, the heating temperature for carbon dioxide removal is preferably 60-120° C., the removal rate of carbon dioxide in the pentanediamine catalytic solution is 30%-80%, and the loss rate of pentanediamine is 0.01%-10.00%.

The strong base is added into the pentanediamine catalytic solution after carbon dioxide is removed to replace the free pentanediamine. Wherein the strong base includes sodium hydroxide, potassium hydroxide or calcium hydroxide, etc. The molar ratio of the amount of the strong base to the pentanediamine content in the catalytic solution is 0.1-5.0:1, preferably 0.5-3.0:1.

After adding the strong base into the pentanediamine catalytic solution, the volatile pentanediamine can be collected by atmospheric distillation, under pressure distillation, rectification, flash distillation, spray drying or reduced pressure drying, etc. wherein the distillation temperature is 40° C.-200° C.; the distillation pressure (absolute pressure) is 0.2 kPa-1100.0 kPa.

The present invention also provides a method for recycling carbon dioxide escaped from the catalytic liquid. Since the pentanediamine catalyst liquid does not contain other acidic gases, a high-purity carbon dioxide can be obtained by liquefaction under pressure on the recycled carbon dioxide; the collected carbon dioxide can be mixed with ammonia to produce urea under heating and pressure reaction conditions; Carbon dioxide neutralizes with a base (such as ammonia aqueous, sodium hydroxide, potassium hydroxide, calcium hydroxide, magnesium hydroxide, sodium carbonate, potassium carbonate, ammonium carbonate, etc.) to generate ammonium carbonate/ammonium bicarbonate, sodium carbonate/sodium bicarbonate, potassium carbonate/potassium bicarbonate, calcium carbonate, magnesium carbonate, sodium bicarbonate, potassium bicarbonate, ammonium bicarbonate, etc.

The pentanediamine whole-cell catalytic solution of the present invention is a catalytic solution obtained at the end of the whole-cell catalytic production of pentanediamine by utilizing the self-controlled pH by by-product carbon dioxide method. The "self-controlled pH by by-product carbon dioxide" is specifically that no acidic pH regulator is added and no gas is introduced into the catalytic solution during the whole cell catalytic process, and the acidic carbon dioxide produced by the lysine decarboxylation reaction is used to neutralize alkaline product pentanediamine.

According to the above-mentioned method of the whole-cell catalytic production process for pentanediamine using self-controlled pH by by-product carbon dioxide, wherein, the by-product carbon dioxide refers to the carbon dioxide that is simultaneously produced along with pentanediamine by lysine under the catalysis of lysine decarboxylase.

In the present invention, acidic carbon dioxide and alkaline pentanediamine are easy to form pentanediamine carbonate in aqueous solution. With the catalytic consumption of lysine substrate in the solution and the formation of pentanediamine carbonate, the pH value of the catalytic solution slowly increased until it is stable. The concentration of the lysine salt substrate can be 20-500 g/L, and the pH value of the catalytic solution does not exceed 8.5 when it is stable, generally does not exceed 8.0.

The cells used for catalyzing the production of pentanediamine according to the present invention refer to a bacteria overexpressing lysine decarboxylase genes.

Wherein the lysine decarboxylase is an enzyme which converts lysine to 1,5-pentanediamine, and examples thereof without special limitation include the enzymes from microorganism such as *Escherichia coli, Bacillus subtilis, Corynebacterium glutamicum, Bacillus halodurans, Selenomonas ruminantium, Hafnia alvei, Vibrio cholera, Streptomyces coelicolor, Streptomyces pilosus, Eubacterium acidaminophilum, Salmonella typhimurium*, or *Pyrococcus abyssi*, and the like. The enzyme from *Escherichia coli* is preferred.

The engineered bacteria for whole-cell catalysis production of pentanediamine according to the present invention is a bacteria overexpressing lysine decarboxylase gene. The bacteria is preferably an *Escherichia coli*, more preferably an *Escherichia coli* B strain or a derivative strain thereof. The overexpressing refers to increasing the amount of the lysine decarboxylase in the cell, the method thereof can specifically be increasing the copy number of the lysine decarboxylase gene, such as carrying all or part of nucleotides sequence of lysine decarboxylase gene using multicopy expression plasmid, or inserting all or part of the nucleotide sequence of the multi-copy lysine decarboxylase gene into the chromosome; the method thereof can also be the application of a highly efficient expression level of the expression-only element-adjust gene, the element can be a strong promoter, enhancer or RBS, etc.; the method thereof can also be modifying gene coding sequences, such as codon optimization, to improve the translation efficiency of lysine decarboxylase.

The engineered bacteria for whole cell catalysis production of pentanediamine can further express the lysine-pentanediamine antiporter gene cadB in an appropriate amount on the basis of overexpression of the lysine decarboxylase gene. The expression of the lysine-pentanediamine antiporter gene cadB in an appropriate amount means that all or part of the nucleotide sequence of the lysine-pentanediamine antiporter gene with or without the RBS sequence is placed after the nucleotide sequence of lysine decarboxylase gene in an exogenous expression plasmid and then expressed; or the promoter of lysine-pentanediamine antiporter gene on the chromosome of the *Escherichia coli* B strain or its derivative strain is replaced by a promoter suitable for *E. coli* to release the transcriptional repression of cadB. The promoter suitable for *E. coli* to release transcriptional repression of cadB is specifically an L promoter, a trc promoter, a T5 promoter, a lac promoter, a tac promoter or a T7 promoter.

A method for preparing 1,5-pentanediamine is also within the protection scope of the present invention, which comprising the following steps: cultivating any of the above-mentioned engineered bacteria in an LB liquid medium to obtain a seed liquid; adding the seed liquid to the rich medium for fermenting and culturing; adding a inducer to induce the expression, then adding the substrates lysine and pyridoxal phosphate to start whole-cell catalysis;

The inducer is specifically IPTG or lactose;

The substrate lysine is specifically a lysine fermentation broth containing lysine producing bacteria, lysine fermentation broth removing bacteria, lysine fermentation broth removing bacteria and decolorizing, ion exchange eluent of lysine fermentation broth, free lysine, lysine salt dry powder or a solution thereof;

The rich medium contains 10 g/L yeast extract, 20 g/L tryptone, 0.9 g/L $K_2HPO_4.3H_2O$, 1.14 g/L $KH_2PO_4$, 10 g/L $(NH_4)_2SO_4$, 0.3 g/L $MgSO_4.7H_2O$, 5 mL/L microelement stock solution, 50 mg/L kanamycin, and water for the balance;

The microelement stock solution contains 6 g/L $FeSO_4.7H_2O$, 1.35 g/L $CaCl_2$, 0.8 g/L $ZnSO_4.7H_2O$, 1.5 g/L $MnSO_4.4H_2O$, 0.15 g/L $CuSO_4.5H_2O$, 0.2 g/L $(NH_4)_6Mo_7O_{24}.4H_2O$, 0.1 g/L $H_3BO_3$, 0.25 g/L $CoCl_2.6H_2O$ and concentrated hydrochloric acid, and water for the balance.

The $OD_{600}$ of the seed liquid is 2-25, and preferably 3-5;

The ratio of the seed liquid to the rich medium is 0.5-30.0%, specifically 5%;

The temperature of the fermentation is 25° C.-45° C., specifically 37° C.;

Dissolved oxygen (DO) of the fermentation is more than 50%;

The pH value of the fermentation is 4.0-9.0;

The final concentration of the IPTG is 0.01-10.00 mM, preferably 0.05-0.40 mM;

The time of adding the IPTG is 2-10 h after fermentation, preferably 2-6 h;

The lysine salt includes L-lysine hydrochloride or lysine sulfate;

The time for starting the whole-cell catalysis by adding substrates lysine and pyridoxal phosphate is 0.5-10 h after induction, preferably 1-5 h after induction;

The catalysis further comprises the following steps: controlling temperature at 25-60° C., stirring speed of 0-1200 rpm;

In the catalytic process, the temperature is specifically 30-50° C.;

In the catalytic process, the stirring speed is specifically 200-1000 rpm.

A method for preparing 1,5-pentanediamine is also within the protection scope of the present invention, which comprising the following steps: cultivating the engineered bacteria according to claims in an LB liquid medium to obtain a seed liquid; adding the seed liquid to the inorganic salt medium for fermenting and culturing; adding a inducer to induce expression, then adding the substrates lysine and pyridoxal phosphate to start whole-cell catalysis;

The inducer is specifically IPTG or lactose;

The substrate lysine is lysine fermentation broth containing lysine producing bacteria, lysine fermentation broth removing bacteria, lysine fermentation broth removing bacteria and decolorizing, ion exchange eluent of lysine fermentation broth, free lysine, lysine salt dry powder or a solution thereof;

The inorganic salt medium contains 2 g/L $(NH_4)_2HPO_4$, 4 g/L $KH_2PO_4$, 0.85 g/L citric acid, 0.7 g/L $MgSO_4.7H_2O$, 10 mg/L $FeSO_4.7H_2O$, 2.25 mg/L $ZnSO_4.7H_2O$, 0.2 mg/L $CuSO_4.5H_2O$, 0.5 mg/L $MnSO_4.5H_2O$, 0.23 mg/L $NaB_4O_7.10H_2O$, 2.0 mg/L $CaCl_2.2H_2O$, 0.1 mg/L $NH_4Mo_7O_{24}$, 0.15 mg/L $CoCl_2.6H_2O$, and water for the balance.

In the above method, the concentration of kanamycin in the LB liquid medium is 5-200 mg/L, specifically 50 mg/L;

The $OD_{600}$ of the seed liquid is 2-25, and preferably 3-5;

The ratio of the seed liquid to the inorganic salt medium is 0.5-30.0%, specifically 2%;

The temperature of the fermentation is 25° C.-45° C., specifically 37° C.;

The DO of the fermentation is more than 50%;

The concentration of glucose during the fermentation is maintained below 5 g/L, specifically by adding feeding liquid, the feeding liquid contains 700 g/L glucose and 20 g/L $MgSO_4.7H_2O$, and water for the balance;

The final concentration of the IPTG is 0.01-10.00 mM, preferably 0.05-0.40 mM;

The time of adding the IPTG is 3-20 h after fermentation, preferably 4-12 h;

The lysine salt comprises L-lysine hydrochloride or lysine sulfate;

The time for starting the whole cell catalysis by adding substrates lysine and pyridoxal phosphate is 0.5-24 h after induction, preferably 1-5 h after induction;

In the catalytic process, the temperature is specifically 30-50° C.;

The stirring speed is specifically 200-1000 rpm.

The substrate lysine is specifically lysine fermentation broth containing lysine producing bacteria, lysine fermentation broth removing bacteria, lysine fermentation broth removing bacteria and decolorizing, ion exchange eluent of lysine fermentation broth, free lysine, lysine salt dry powder or its solution; wherein the lysine salts are the reaction products of lysine and organic or inorganic acids, such as lysine hydrochloride, lysine sulfate, lysine carbonate, lysine acetate, lysine adipate, lysine succinate or lysine sebacate.

The beneficial effects of the present invention are as follows:

Firstly, the content of carbonate (bicarbonate) ion in the catalytic solution is reduced by removing carbon dioxide from the catalytic solution of pentanediamine, and the amount of the strong base used to replace pentanediamine in the process of separation and extraction of pentanediamine is reduced, correspondingly, the amount of salt residue formed after volatilization of pentanediamine is reduced, thereby reducing the cost of auxiliary materials and the cost of waste residue treatment in pentanediamine production;

Secondly, the removal of carbon dioxide can avoid the problems of blockage of the pipeline, yield reduction and the like, which brought by the condensation in the outlet or the pipeline of the heating vessel caused by carbon dioxide and the gaseous pentanediamine neutralization due to insufficient base amount in the distillation process of pentanediamine;

Thirdly, by reasonably controlling the carbon dioxide removal conditions, pentanediamine is prevented from being largely distilled off during the process of removing carbon dioxide, resulting in lower product yield and higher production cost;

Finally, the present invention provides a method for capturing and utilizing of carbon dioxide, the by-products of lysine decarboxylation, which not only reduces greenhouse gas emissions, but also generates additional economic benefits.

In summary, the technology of the present invention is applicable to the industrial production of 1,5-pentanediamine in practice, and has high practicability and applicability.

For ease of understanding, the present invention will be described in detail below through the specific drawings and embodiments. It should be noted in particular that these descriptions are merely illustrative descriptions and do not constitute a limitation on the scope of the invention. According to the description, many changes and modifications of the present invention are obvious to those person skilled in the art.

In addition, the present invention refers to the published literatures to describe the present invention more clearly, and these literatures are incorporated here for reference as if their full-texts have been repeated in this article.

DETAILED DESCRIPTION OF EMBODIMENT

The experimental methods used in the following embodiments are conventional methods unless with special description. Materials, reagents, etc. used in the following embodiments are commercially available unless otherwise specified.

Embodiment 1 Detection of Lysine and Pentanediamine by HPLC 1 mL whole-cell catalytic solution is centrifuged at 8000 g for 5 min, and the supernatant is collected to detect lysine content; 10 μL supernatant is added into 2 mL centrifugal tube, and 200 μL 0.5 mol/L $NaHCO_3$ aqueous solution and 100 μL 1% (volume ratio) dinitrofluorobenzene acetonitrile solution were added, and heated for 60 min in the dark area of the water bath at 6° C., then cooled to room temperature. 700 μL 0.04 mol/L $KH_2PO_4$ aqueous solution (pH=7.2±0.05, pH value is adjusted with 40 g/L KOH aqueous solution) was added to dilute, and then shake well. The sample can be injected after keeping for 15 min and filtration, and the injection volume is 15 μL;

The chromatographic column used is C18 column (ZORBAX Eclipse XDB-C18, 4.6*150 mm, Agilent, USA); column temperature: 40° C.; ultraviolet detection wavelength: 360 nm; mobile phase A is 0.04 mol/L $KH_2PO_4$ (pH=7.2+0.05, adjusted by 40 g/100 mL KOH solution), mobile phase B is 55% (volume ratio) acetonitrile aqueous solution, the total flow rate of mobile phase is 1 mL/min. The elution process is as follows:

At the beginning of elution (0 min), the volume fraction of mobile phase A in the total flow of the mobile phase is 86%, and volume fraction of mobile phase B in the total flow of the mobile phase is 14%; The elution process is divided into five stages, the volume fraction of mobile phase A and mobile phase D in the total flow of the mobile phase are linearly changed in each stage; the volume fraction of mobile phase A in the total flow of the mobile phase is 88%, and the volume fraction of mobile phase B in total flow of the mobile phase is 12% at the end of the first stage (conducting for 2 min from the beginning). The volume fraction of mobile phase A in the total flow of the mobile phase is 86%, and the volume fraction of mobile phase B in total flow of the mobile phase is 14% at the end of the second stage (conducting for 2 min from the end of the first stage). The volume fraction of mobile phase A in the total flow of the mobile phase is 70%, and the volume fraction of mobile phase B in total flow of the mobile phase is 30% at the end of the third stage (conducting for 6 min from the end of the second stage). The volume fraction of mobile phase A in the total flow of the mobile phase is 30%, and the volume fraction of mobile phase B in total flow of the mobile phase is 70% at the end of the fourth stage (conducting for 10 min from the end of the third stage). A standard curve is prepared using a commercially available L-lysine standard, then calculate the lysine concentration of the sample.

In the detection of pentanediamine, 10 μL sample supernatant is added into a 2 mL centrifugal tube containing 100 μL 4.2 g/100 mL sodium bicarbonate aqueous solution. After blending, 200 μL acetonitrile solution containing 2,4-dinitrofluorobenzene with volume percentage of 1% is added and mixed. And then keeping the derivatization reaction for 60 min at 60° C. (strictly timing, take out the centrifugal tube for slight oscillation and blending at 30 min, and then continue the derivatization reaction). Taking out the centrifugal tube and cooling to room temperature in the dark. Swirl shaking and mixing for 30 s after adding 1600 μL acetonitrile. After filtration with organic filter membrane, the sample can be injected, and the injection volume is 15 μL.

The mobile phase A is 5.4 g/L potassium dihydrogen phosphate aqueous solution with pH 7.2 and the mobile phase B is acetonitrile aqueous solution with volume percentage of 80%. A and B are pumped into the mobile phase at a flow rate of 1 mL/min at a volume ratio of 5:95. The chromatographic column used is C18 (ZORBAX Eclipse XDB-C18, 4.6*150 mm, Agilent, USA); column temperature: 35° C.; detection wavelength: 360 nm.

1,5-pentanediamine hydrochloride (purchased from Sigma company) is used as standard, the concentration of 1,5-pentanediamine hydrochloride has a good linearity between 1-5 g/L. The standard curve is prepared by taking the concentration of the standard as the abscissa and the integral peak area of the standard as the ordinate.

The concentration of 1,5-pentanediamine in the following embodiments is converted from the measured value of 1,5-pentanediamine hydrochloride calculated by the standard curve formula.

Embodiment 2 Construction of Engineered Bacteria for Whole-Cell Catalytic Production of Pentanediamine (I) Construction of Overexpression Plasmid Comprising Lysine Decarboxylase Gene cadA The ORF of the optimized lysine decarboxylase gene cadA was inserted after the T7 promoter and RBS of the pET28a(+) expression vector. The primers were designed using the optimized sequence of cadA, and the genomic DNA of the wild-type Escherichia coli K12 W3110 strain was used as a template. The cadA gene was amplified by PCR using the high-fidelity polymerase KAPA HiFi™ HotStar with P1 and P2 as primers. The nucleotide sequence of this gene is shown in SEQ ID NO. 1. The PCR procedure was performed for a total of 26 cycles, with each cycle including: denaturation at 98° C. for 30 seconds, annealing at 65° C. for 15 seconds, and extension at 72° C. for 150 seconds. A mutation site was introduced by primer P1 to obtain a fragment of the engineered lysine decarboxylase gene cadA*

```
P1:
                                            (SEQ ID NO. 5)
5-CATGCCATGGCAGTTATTGCAATATTGAATCATATGGGAGT
(The underlined sequence is the restriction
recognition site of Nco I)

P2:
                                            (SEQ ID NO. 6)
5'-ACGCGTCGACCTCCTTATGAGCAAAAAAGGGAAGTG-3'
(The underlined sequence is the restriction
recognition site of Sal I)
```

Figure 1:
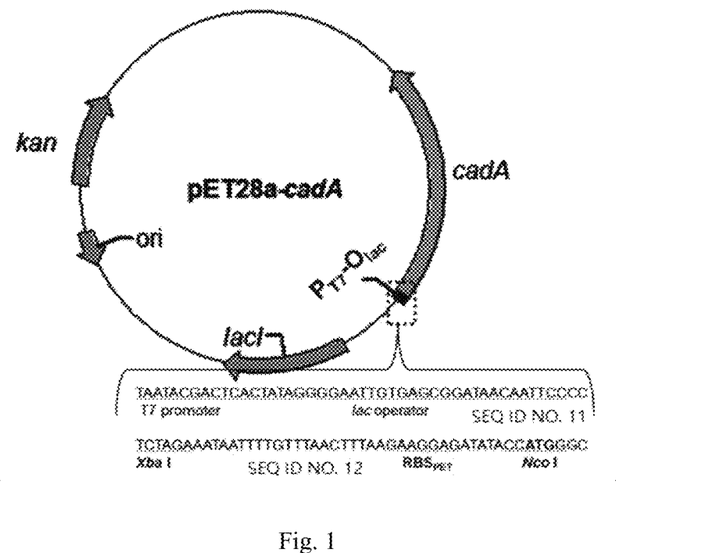
FIG. 1 is plasmid profile of pET28a-cadA.

The electrophoresis band of PCR products was recovered by gel extraction, and the DNA fragment of lysine decarboxylase gene cadA* and pET28a(+) plasmid were digested with restriction endonucleases Nco I and Sal I to obtain lysine decarboxylase gene cadA* gene fragment and large vector fragment after Enzyme digestion. The digested lysine decarboxylase gene cadA* gene fragment was ligated to the large vector fragment and transformed into competent cells of E. coli EC135 (Zhang et al, Plos Genetics, 2012, 8(9): e1002987). The LB plates containing 50 mg/L kanamycin were screened to obtain a transformant containing the recombinant plasmid, and the plasmid of which was extracted and sequenced. The plasmid with correct result was named pET28a-cadA* and shown in FIG. 1.

(II) Replacement of the Promoter of Chromosomal cadB Gene.

The genomic DNA of Escherichia coli BL21 (DE3) strain was used as a template, and PCR amplification was performed with primers P3 and P4, P5 and P6 respectively, and two DNA fragments of 510 bp and 610 bp in length were obtained, respectively, as shown in SEQ ID No. 2 and SEQ ID No. 3, respectively. Among them, the T7 promoter sequence and the lac regulatory sequence were introduced by primers P4 and P5. The PCR was performed as follows: denaturation at 94° C. for 30 s, annealing at 52° C. for 30 s, and extension at 72° C. for 30 s (30 cycles in total). As used herein, the primer sequence is as follows:

```
P3:
                                            (SEQ ID NO. 7)
5'-CGCGGATCCTGCGCCATTCTCAACATCCTT-3'
(The underlined sequence is the restriction
recognition site of BamHI)

P4:
                                            (SEQ ID NO. 8)
5'-TCCGCTCACAATTCCCCTATAGTGAGTCGTATTATGCCGCAACATATT
ATACCAACAG-3'

P5:
                                            (SEQ ID NO. 9)
5'-ACTCACTATAGGGGAATTGTGAGCGGATAACAATTCCGAAATTAGGAG
AAGAGCATGAG-3'

P6:
                                            (SEQ ID NO. 10)
5'-ATTGCGGCCGC TCCGCAGTATTCCAGTTAGCT-3'
(The underlined sequence is the restriction
recognition site of Not I)
```

A mixture of DNA molecules represented by SEQ ID No. 2 and SEQ ID No. 3 was used as a template, and P3 and P6 were used as primers, thereby an Overlap fragment of about 1.1 kb in length was amplified by Overlap PCR. The sequence of overlap fragment was shown in SEQ ID No. 4. The PCR procedure was performed for a total of 26 cycles, with each cycle including: denaturation at 94° C. for 30 seconds, annealing at 52° C. for 30 seconds, extension at 72° C. for 60 seconds.

The sequence shown in nucleotides 477$^{th}$ to 495$^{th}$ from the 5' end in SEQ ID No. 4 is the T7 promoter sequence, and the sequence shown in nucleotides 496$^{th}$ to 520$^{th}$ from the 5' end in SEQ ID No. 4 is the lac regulatory sequence.

Bam HI and Not I cleave the DNA molecule of SEQ ID No. 3 to obtain a gene fragment; while Bam HI and Not I cleave the pKOV plasmid to obtain a large fragment of the vector. The gene fragment was ligated to the large vector fragment to obtain a recombinant plasmid named pKOV-PT7-cadB. The recombinant plasmid was sequenced and verified the present of correct T7 promoter and lac regulatory gene sequences, and stored for later use.

The constructed pKOV-PT7-cadB plasmid was electrotransformed into E. coli BL21 (DE3) strain and resuscitated in LB medium for 2 h at 30° C., 150 rpm. Monoclones positive for homologous recombination were selected according to the commercial guidelines for the pKOV plasmid of Addgene. It was confirmed by sequencing that its own promoter of the cadB gene on the chromosome was replaced by the T7 promoter, and the strain was named E. coli BL21 PcadB:: PT7.

(3) Construction of Engineered Bacteria for Pentanediamine

The plasmid pET28a-cadA* is transformed into competent cells of E. coli BL21 P$_{cadB}$:: P$_{T7}$. The engineered bacteria E. coli BL21 P$_{cadB}$:: PT7/pET28a-cadA* is screened on LB plates containing 50 mg/L kanamycin for whole-cell catalysis of 1,5-pentanediamine.

Embodiment 3 Bacterial Culture and Catalytic Production of Pentanediamine

Scraping engineered bacteria E. coli BL21 (DE3) P$_{cadB}$:: P$_{T7}$/pET28a-cadA* and inoculating into a 500 mL triangular flask containing 50 mL LB medium (containing 50 mg/L kanamycin (it can be 5-200 mg/L)), and culturing in shaker for 4 h at 37° C. and 220 rpm to obtain seed liquid, and OD$_{600}$ is 4-5. The obtained seed liquid is inoculated into the 10 L fermentation tank containing 2 L inorganic salt medium at an inoculum concentration of 2%, and the culture temperature is 37° C., DO is more than 30%, and the tank pressure is 0.02-0.10 MPa. The concentration of glucose in the culture solution is maintained below 5 g/L by adding feeding liquid. When the OD$_{600}$ of the bacteria in the culture medium is 30-40, adding 0.1 mM inducer IPTG. After 2 h, the OD$_{600}$ of the bacteria in the culture medium is about 80, and the wet cells are obtained by centrifugation.

Wherein, the compositions of inorganic salt medium and feeding liquid are as follows: inorganic salt medium: 2 g/L (NH$_4$)$_2$HPO$_4$, 4 g/L KH$_2$PO$_4$, 0.85 g/L citric acid, 0.7 g/L MgSO$_4$.7H$_2$O, 10 mg/L FeSO$_4$.7H$_2$O, 2.25 mg/L ZnSO$_4$.7H$_2$O, 0.2 mg/L CuSO$_4$.5H$_2$O, 0.5 mg/L MnSO$_4$.5H$_2$O, 0.23 mg/L NaB$_4$O$_7$.10H$_2$O, 2.0 mg/L CaCl$_2$.2H$_2$O, 0.1 mg/L NH$_4$Mo$_7$O$_{24}$, 0.15 mg/L CoCl$_2$.6H$_2$O, and water for the balance. The feeding liquid contains 700 g/L glucose and 20 g/L MgSO$_4$.7H$_2$O, and water for the balance.

Figure 2:
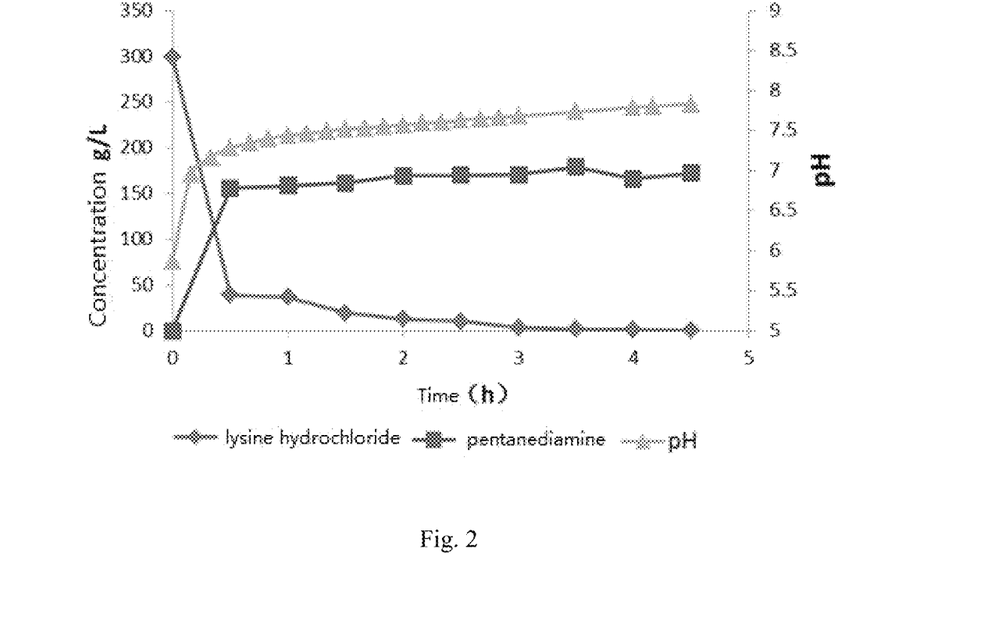
FIG. 2 is the process curve of whole-cell catalysis for the production of pentanediamine.

A catalytic liquid system containing 300 g/L lysine hydrochloride and 0.2 mmol/L PLP is prepared. After adjusting the temperature to 37° C., the stirring speed of fermentation tank is set to 500 rpm, and the whole-cell catalysis is started by adding 20 g/L wet bacteria (equivalent to cell dry weight of 4 g/L). The pH of the self-regulating catalytic system is adjusted by the by-product CO$_2$ without adjusting the pH by adding acidic substances and without air supply. In the first 20 min of the start of the catalysis, the pH value rapidly increases to about 7.2, and then slowly increases to 7.8 in the next few hours (FIG. 2). The catalytic solution is taken out from the fermenter tank every 0.5 h, centrifuged at 12000×g for 5 min, and the supernatant is decanted. The yield of 1,5-pentanediamine in the whole-cell catalysis process is detected according to the lysine and -pentanediamine method in embodiment 1. As shown in FIG. 2, the trend of lysine consumption and pentanediamine production is similar to that of pH value. The lysine is rapidly consumed in the first 0.5 h and the pentanediamine is rapidly accumulated, and then the change of the process is slow. The catalytic consumption rate of the substrate is 99.8% after catalyzing for 4 h, and the residual lysine hydrochloride is only 0.67 g/L.

Embodiment 4 Removal of Carbon Dioxide in Pentanediamine Catalytic Solution by Distillation Under Reduced Pressure The bacteria in the catalytic reaction solution are removed by centrifugation. Adding 500 mL of the centrifuged pentanediamine catalyst solution to the round bottom flask in the 20 L oil bath rotary evaporator, and carbon dioxide is removed by distillation under reduced pressure. In the process of carbon dioxide desorption, the vacuum meter reading of the circulating water vacuum pump reaches to about −0.095 Mpa, and the heating temperature of the water bath is set to 60° C., 70° C., 80° C., 90° C., 100° C., 120° C., 140° C. and 160° C., respectively, and then investigating the removal of carbon dioxide at different temperatures. After the pressure and temperature are stable, distillation under reduced pressure is carried out for 60 min. After the distillation, adding the ultra-pure water to the circular bottom flask, and fixing to the initial volume to determine the carbon dioxide content in the pentanediamine catalytic solution before and after the distillation. The total inorganic carbon (TIC) content of the catalytic solution is detected by the total organic carbon total nitrogen analyzer (Vario TOC) to calculate the carbon dioxide removal rate of the catalytic reaction solution. The calculation formula is as follows: the removal rate of carbon dioxide=(TIC content of the pentanediamine catalytic solution before distillation under reduced pressure−TIC content in the pentanediamine catalytic solution after distillation under reduced pressure)/TIC content of the pentanediamine catalytic solution before distillation under reduced pressure×100%. The experimental results show that the removal rate of carbon dioxide in the pentanediamine catalytic solution increases with the increase of heating temperature (Table 1).

TABLE 1

Carbon dioxide removal rate of pentanediamine catalytic solution at different temperatures for distillation under reduced pressure

| Temperature (° C.) | Removal rate of CO$_2$ (%) |
| --- | --- |
| 60 | 42.9 |
| 70 | 48.7 |
| 80 | 53.1 |
| 90 | 57.1 |
| 100 | 59.3 |
| 120 | 66.6 |
| 140 | 68.9 |
| 160 | 80.2 |

During the removal of carbon dioxide, pentanediamine will also volatilize. In the distillation process under reduced pressure with different temperatures mentioned above, the temperature of the cooling circulating water is set to 20° C.

Collecting the condensed fraction to detect the content of pentanediamine, and calculating the loss rate of pentanediamine in the carbon dioxide removal process. The calculation method is as follows: the loss rate of pentanediamine= (fraction pentanediamine content×fraction volume)/ (pentanediamine content of the catalytic solution before distillation×volume of the catalytic solution added to the round bottom flask)×100%. The results are shown in Table 2: the loss rate of pentanediamine increases with the increase of distillation temperature. When the heating temperature is set to 60° C., the loss rate of pentanediamine is less than 0.1%; and when the heating temperature is raised to 160° C., the loss rate of pentanediamine reaches to 8% or more. When the heating temperature is higher than 120° C., a large amount of pentanediamine volatilizes and escapes, and coagulates with the carbon dioxide gas into milky white pentaneamine carbonate on the surface of equipment pipe with lower temperature, which not only easily clogs the pipeline, but also increases the difficulty of equipment cleaning.

TABLE 2

Loss rate of penanediamine at different temperatures for distillation under reduced pressure

| Temperature (° C.) | Loss rate of penanediamine (%) |
|---|---|
| 60 | 0.06 |
| 70 | 0.09 |
| 80 | 0.35 |
| 90 | 0.96 |
| 100 | 1.22 |
| 120 | 3.07 |
| 140 | 4.13 |
| 160 | 8.16 |

Embodiment 5 Recycling the Removed Carbon Dioxide by Alkaline Solution

Figure 3:
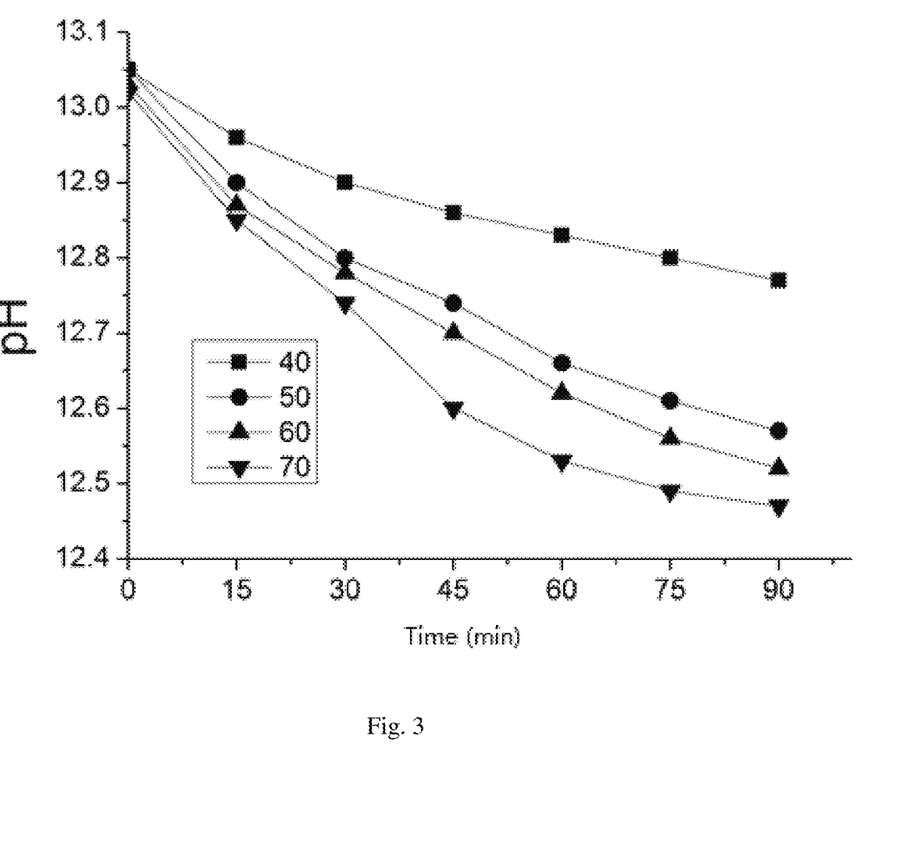
FIG. 3 is the change curve of pH value during the process of recycling carbon dioxide by alkaline solution.

The bacteria in the catalytic reaction solution are removed by centrifugation. Adding 500 mL of the centrifuged pentanediamine catalyst solution to the round bottom flask of the 5 L rotary evaporator, and carbon dioxide is removed by distillation under reduced pressure. In the process of distillation, the vacuum meter reading of the circulating water vacuum pump is about −0.095 Mpa, and the heating temperature of the water bath is set to 40° C., 50° C., 60° C. and 70° C., respectively, and then investigating the removal of carbon dioxide at different temperatures. Adding 10 L sodium hydroxide solution with content of 6 g/L to the circulating water vacuum pump tank for absorbing carbon dioxide desorbed in the pentanediamine catalyst solution. The pH electrode is inserted into the tank to record the pH value of the alkaline solution of the circulating water vacuum pump tank in real time. As the removed carbon dioxide is chemically absorbed in the alkaline solution, the pH of the alkaline solution in the tank gradually decreases. The higher the heating temperature is, the faster the pH value of the alkaline solution in the tank decreases (FIG. 3).

Figure 4:
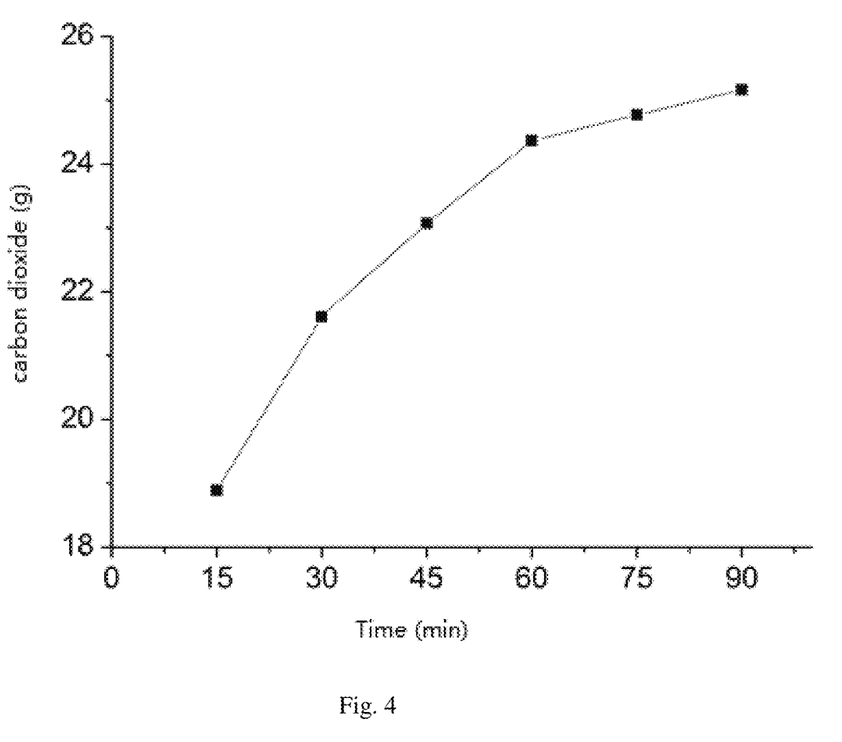
FIG. 4 is the process curve of the removal of carbon dioxide.

The total inorganic carbon (TIC) content of the alkaline solution of the circulating water vacuum pump tank is detected by the total organic carbon total nitrogen analyzer (type of Vario TOC) to calculate the absorption amount of carbon dioxide absorbed by alkaline solution. When the heating temperature of vacuum distillation is 50° C., the process curve of carbon dioxide absorption by the alkaline solution is shown in FIG. 4. The content of TIC of the alkaline solution in the circulating water vacuum pump tank increases gradually.

Embodiment 6 the Reduced Consumption of Strong Base to Replace Free Pentanediamine by Removal of Carbon Dioxide After the carbon dioxide is removed by the temperature and pressure conditions of embodiment 5 for 90 min, the pentanediamine catalyst solution is poured out from the round bottom flask and diluted with ultrapure water to 2 L, and then measuring the pH value of the diluted catalytic solution. When the heating temperature of the water bath is set to 40° C., 50° C., 60° C. and 70° C. for the removal of carbon dioxide, the pH value of the catalytic liquid rises from 7.66 to 8.45, 9.63, 9.75 and 9.90, respectively. Further, adjusting the pH value of the pentanediamine catalytic solution diluted to the equal volume with sodium hydroxide. After removing carbon dioxide, the pH of the catalytic solution of 100 mL is set to 11, 12 and 13, respectively, which need 42 mL, 72 mL and 106 mL of sodium hydroxide solution (100 g/L) respectively. While before the removal of carbon dioxide, diluting the catalyst solution with the same content of pentanediamine consumed 97 mL, 141 mL and 185 mL of sodium hydroxide solution, respectively. The results show that in the process of replacing free pentanediamine with strong base, the removal of carbon dioxide from the catalytic solution can significantly reduce the amount of strong base, and the amount of the formed solid residue after distillation of pentanediamine is much less.

Embodiment 7 the Removal of Carbon Dioxide Improves the Distillation Yield of Pentanediamine The bacteria in the catalytic reaction solution are removed by centrifugation. Adding 500 mL of the centrifuged pentanediamine catalyst solution to the round bottom flask in the 20 L rotary evaporator. The temperature of oil bath is set to 70° C. and the carbon dioxide is removed by distillation under reduced pressure. After 90 min, the sodium hydroxide with equivalent amount is added. The temperature of oil bath is set to 120° C., and the distillation under reduced pressure is continued for 120 min to collect the pentanediamine fraction. In the control experiment, the carbon dioxide is not removed, and the pentanediamine catalyst solution with the equivalent amount of sodium hydroxide is distilled directly under the same conditions to collect the pentanediamine fraction. After removal of carbon dioxide, 62.3 g of pentanediamine can be obtained by the distillation of the pentanediamine catalytic solution with the replacement of strong base, whereas only 11.8 g of pentanediamine could be obtained in the control experiment.

What is claimed is:

1. A method for preparing 1,5-pentanediamine by fermentation, consisting of the steps of:
   (1) culturing a cell overexpressing a lysine decarboxylase and adding the substrates lysine and pyridoxal phosphate to start whole-cell catalysis to obtain a fermentation broth comprising 1,5-pentanediamine, wherein the cell is a cell whose expression is enhanced by replacing the promoter of the lysine decarboxylase gene with T7 promoter, and the cell is *E. coli* BL21 (DE3), and no acidic pH regulator is added to the fermentation broth, wherein the cells themselves generate $CO_2$, to neutralize 1,5-pentanediamine;
   (2) removing the cells in the fermentation broth to obtain a clear liquid of fermentation broth;
   (3) removing carbon dioxide from the liquid obtained in step (2) by distillation under reduced pressure at about −0.095 MPa and at a temperature from 60° C. to 70° C., and then adding a base to obtain a treatment liquid; and
   (4) extracting a composition containing 1,5-pentanediamine from the treatment liquid obtained in the step (3) by distillation under the reduced pressure.

2. The method according to claim 1, wherein in step (2), the removing is centrifuging or filtering.

3. The method according to claim 1, wherein in step (3), the base includes sodium hydroxide, potassium hydroxide and/or calcium hydroxide.

4. The method according to claim 1, wherein the prepared 1,5-pentanediamine is greater than 30 g/L of the fermentation broth.

5. The method according to claim 4, wherein the prepared 1,5-pentanediamine is greater than 50 g/L of the fermentation broth.

6. The method according to claim 5, wherein the prepared 1,5-pentanediamine is greater than 80 g/L of the fermentation broth.

7. The method according to claim 6, wherein the prepared 1,5-pentanediamine is greater than 100 g/L of the fermentation broth.

8. The method according to claim 7, wherein the prepared 1,5-pentanediamine is greater than 120 g/L of the fermentation broth.

* * * * *